(12) United States Patent
Bernhard et al.

(10) Patent No.: US 10,537,278 B2
(45) Date of Patent: Jan. 21, 2020

(54) APPARATUSES FOR DETECTING AND/OR DIAGNOSING SWALLOWING DISORDERS

(71) Applicant: NESTEC S.A., Vevey (CH)

(72) Inventors: Hans Bernhard, Liebefeld (CH); Elise Gortchacow, Wabern (CH); Michael Jedwab, Lausanne (CH); Adam Burbidge, Arzier (CH)

(73) Assignee: Societe des Produits Nestle S.A., Vevey (CH)

( * ) Notice: Subject to any disclaimer, the term of this patent is extended or adjusted under 35 U.S.C. 154(b) by 9 days.

(21) Appl. No.: 14/406,974

(22) PCT Filed: Jun. 19, 2013

(86) PCT No.: PCT/EP2013/062820
§ 371 (c)(1),
(2) Date: Dec. 10, 2014

(87) PCT Pub. No.: WO2013/190021
PCT Pub. Date: Dec. 27, 2013

(65) Prior Publication Data
US 2015/0112150 A1  Apr. 23, 2015

Related U.S. Application Data

(60) Provisional application No. 61/661,639, filed on Jun. 19, 2012.

(51) Int. Cl.
*A61B 5/00* (2006.01)
*A61B 5/11* (2006.01)
*A61B 7/00* (2006.01)

(52) U.S. Cl.
CPC .............. *A61B 5/4205* (2013.01); *A61B 5/11* (2013.01); *A61B 5/6822* (2013.01);
(Continued)

(58) Field of Classification Search
CPC .................. A61B 5/4205; A61B 5/683; A61B 2560/0285; A61B 5/11; A61B 5/6822;
(Continued)

(56) References Cited

U.S. PATENT DOCUMENTS 5,598,845 A * 2/1997 Chandraratna .......... A61B 8/08
600/459
6,491,647 B1 * 12/2002 Bridger .................. A61B 5/021
128/900

(Continued)

FOREIGN PATENT DOCUMENTS

EP  2108313  10/2009
JP  2006218305  8/2006
(Continued)

OTHER PUBLICATIONS

Japanese Office Action for Application No. P2015-517755, Dispatch No. 078815, Dispatch Date Feb. 28, 2017, 6 pages.

*Primary Examiner* — Lynsey C Eiseman
*Assistant Examiner* — Amanda L Steinberg
(74) *Attorney, Agent, or Firm* — K&L Gates LLP (57) ABSTRACT

Apparatuses for detecting swallowing disorders and methods for using same are provided. In a general embodiment, the apparatuses include a disposable sensor base and a sensor that is received by the disposable sensor base. The sensor base includes a sensor interface having a predetermined cut-away shape and a directionally-keyed mating surface. The sensor includes a handle portion having a shape that corresponds to the predetermined shape of the sensor interface, a support portion configured to be received by the directionally-keyed mating surface when the sensor is inserted into the sensor interface, and electronics configured to collect data sensed by the sensor. The apparatuses of the present disclosure can be attached to a patient's neck to
(Continued)

detect and/or diagnose swallowing disorders during a swallowing test.

20 Claims, 3 Drawing Sheets

(52) U.S. Cl.
CPC .......... *A61B 5/6831* (2013.01); *A61B 5/7282* (2013.01); *A61B 7/008* (2013.01)

(58) Field of Classification Search
CPC .... A61B 5/6831; A61B 5/7282; A61B 5/6838
See application file for complete search history.

(56) References Cited

U.S. PATENT DOCUMENTS

| | | | | |
|---|---|---|---|---|
| 2005/0113703 A1* | 5/2005 | Farringdon | .......... | A61B 5/0428 600/509 |
| 2005/0245839 A1* | 11/2005 | Stivoric | ............. | G06F 19/3418 600/549 |
| 2006/0184051 A1* | 8/2006 | Hempstead | ........ | A61B 5/02028 600/485 |
| 2006/0200020 A1* | 9/2006 | Brister | ................. | A61B 5/0031 600/345 |
| 2007/0123952 A1* | 5/2007 | Strother | ............... | A61N 1/0456 607/48 |
| 2009/0054980 A1* | 2/2009 | Ludlow | .............. | A61H 23/0245 623/9 |
| 2009/0093687 A1* | 4/2009 | Telfort | ................. | A61B 5/0002 600/300 |
| 2012/0046641 A1* | 2/2012 | Jedwab | .................. | A61B 5/00 604/503 |
| 2013/0030257 A1* | 1/2013 | Nakata | ................. | A61B 5/4836 600/301 |

FOREIGN PATENT DOCUMENTS

| | | | | |
|---|---|---|---|---|
| JP | 2008246204 | 10/2008 | | |
| JP | 2010507456 | 3/2010 | | |
| JP | 2011525409 | 9/2011 | | |
| WO | 2008057884 | 5/2008 | | |
| WO | 2011047207 | 4/2011 | | |
| WO | WO 2011047207 A2 * | 4/2011 | ............. | A61B 7/003 |
| WO | 2012101514 | 8/2012 | | |

\* cited by examiner

APPARATUSES FOR DETECTING AND/OR DIAGNOSING SWALLOWING DISORDERS

CROSS REFERENCE TO RELATED APPLICATIONS

The present application is a National Stage of International Application No. PCT/EP2013/062820, filed on Jun. 19, 2013, which claims priority to U.S. Provisional Application Ser. No. 61/661,639, filed on Jun. 19, 2012, the entire contents of which are being incorporated herein by reference.

BACKGROUND

The present disclosure is directed to diagnostic apparatuses. More specifically, the present disclosure is directed to apparatuses for detecting or diagnosing swallowing disorders.

Dysphagia is the medical term for the symptom of difficulty in swallowing. Epidemiological studies estimate a prevalence rate of 16% to 22% among individuals over 50 years of age.

Esophageal dysphagia affects a large number of individuals of all ages, but is generally treatable with medications and is considered a less serious form of dysphagia. Esophageal dysphagia is often a consequence of mucosal, mediastinal, or neuromuscular diseases. Mucosal (intrinsic) diseases narrow the lumen through inflammation, fibrosis, or neoplasia associated with various conditions (e.g., peptic stricture secondary to gastroesophageal reflux disease, esophageal rings and webs, esophageal tumors, chemical injury, radiation injury, infectious esophagitis, and eosinophilic esophagitis). Mediastinal (extrinsic) diseases obstruct the esophagus by direct invasion or through lymph node enlargement associated with various conditions (tumors, infections, and cardiovascular). Neuromuscular diseases may affect the esophageal smooth muscle and its innervation, disrupting peristalsis or lower esophageal sphincter relaxation, or both, commonly associated with various conditions (achalasia, scleroderma, other motility disorders, and a consequence of surgery). It is also common for individuals with intraluminal foreign bodies to experience acute esophageal dysphagia.

Oral pharyngeal dysphagia, on the other hand, is a very serious condition and is generally not treatable with medication. Oral pharyngeal dysphagia also affects individuals of all ages, but is more prevalent in older individuals. Worldwide, and oral pharyngeal dysphagia affects approximately 22 million people over the age of 50. Oral pharyngeal dysphagia is often a consequence of an acute event, such as a stroke, brain injury, or surgery for oral or throat cancer. In addition, radiotherapy and chemotherapy may weaken the muscles and degrade the nerves associated with the physiology and nervous innervation of the swallow reflex. It is also common for individuals with progressive neuromuscular diseases, such as Parkinson's Disease, to experience increasing difficulty in swallowing initiation. Representative causes of oropharyngeal dysphagia include those associated neurological illnesses, infectious illnesses, autoimmune illnesses, metabolic illnesses, myopathic illnesses, iatrogenic illnesses, post surgical muscular or neurogenic, radiation therapy, corrosive, and structural illnesses.

Dysphagia has major consequences on patient health and healthcare costs. Individuals with more severe dysphagia generally experience a sensation of impaired passage of food from the mouth to the stomach, occurring immediately after swallowing. Among community dwelling individuals, perceived symptoms may bring patients to see a doctor. Among institutionalized individuals, health care practitioners may observe symptoms or hear comments from the patient or his/her family member suggestive of swallowing impairment and recommend the patient be evaluated by a specialist. As the general awareness of swallowing impairments is low among front-line practitioners, dysphagia often goes undiagnosed and untreated. Yet, through referral to a swallowing specialist (e.g., speech language pathologist), a patient can be clinically evaluated and dysphagia diagnosis can be determined.

The general awareness of swallowing impairments is low among front-line practitioners. Many people (especially those who are elderly) suffer with undiagnosed and untreated swallowing impairments. One reason is that front-line community care practitioners (e.g., general practitioners/geriatricians, home care nurses, physical therapists, etc.) do not typically screen for the condition. If they are aware of the severity of swallowing impairments, they commonly do not use an evidence-based method of screening. Furthermore, office-based assessment of dysphagia rarely occurs.

Severity of dysphagia may vary from: (i) minimal (perceived) difficulty in safely swallowing foods and liquids, (ii) an inability to swallow without significant risk for aspiration or choking, and (iii) a complete inability to swallow. Commonly, the inability to properly swallow foods and liquids may be due to food boluses being broken up into smaller fragments, which may enter the airway or leave unwanted residues in the oropharyngeal and/or esophageal tract during the swallowing process (e.g., aspiration). If enough material enters the lungs, it is possible that the patient may drown on the food/liquid that has built up in the lungs. Even small volumes of aspirated food may lead to bronchopneumonia infection, and chronic aspiration may lead to bronchiectasis and may cause some cases of asthma.

A common condition among elderly, is the aspiration of the oropharyngeal contents during sleep. People may compensate for less-severe swallowing impairments by self-limiting the diet. The aging process itself, coupled with chronic diseases such as hypertension or osteoarthritis, predisposes elderly to (subclinical) dysphagia that may go undiagnosed and untreated until a clinical complication such as pneumonia, dehydration, malnutrition (and related complications) occurs. Yet, the differential diagnosis of 'aspiration pneumonia' is not necessarily indicated as a result of current care practices.

The economic costs of dysphagia are associated with hospitalization, re-hospitalization, loss of reimbursement due to pay for performance, infections, rehabilitation, loss of work time, clinic visits, use of pharmaceuticals, labor, care taker time, childcare costs, quality of life, increased need for skilled care. Dysphagia and aspiration impact quality of life, morbidity and mortality. Twelve-month mortality is high (45%) among individuals in institutional care who have dysphagia and aspiration. The economic burden of the clinical consequences arising from lack of diagnosis and early management of dysphagia are significant.

Pneumonia is a common clinical consequence of dysphagia. The condition often requires acute hospitalization and emergency room visits. Among those that develop pneumonia due to aspiration, the differential diagnosis of 'aspiration pneumonia' is not necessarily indicated as a result of current care practices. Based on U.S. healthcare utilization surveys from recent years, pneumonia accounted for over one million hospital discharges and an additional 392,000 were attributable to aspiration pneumonia. Individuals who have general pneumonia as the principal diagnosis have a mean 6 day hospital length of stay and incur over $18,000 in costs for hospital care. It is expected that aspiration pneumonia would carry higher costs for hospital care, based on a mean 8 day length of hospital stay. In addition, an acute insult such as pneumonia often initiates the downward spiral in health among elderly. An insult is associated with poor intakes and inactivity, resulting in malnutrition, functional decline, and frailty. Specific interventions (e.g., to promote oral health, help restore normal swallow, or reinforce a swallow-safe bolus) would benefit persons at risk for (due to aspiration of oropharyngeal contents, including silent aspiration) or experiencing recurrent pneumonia.

Similar to pneumonia, dehydration is a life-threatening clinical complication of dysphagia. Dehydration is a common co-morbidity among hospitalized individuals with neurodegenerative diseases (thus, likely to have a swallowing impairment). The conditions of Alzheimer's disease, Parkinson's disease, and multiple sclerosis account for nearly 400,000 U.S. hospital discharges annually, and up to 15% of these patients suffer dehydration. Having dehydration as the principal diagnosis is associated with a mean 4 day length of hospital stay and over $11,000 in costs for hospital care. Nevertheless, dehydration is an avoidable clinical complication of dysphagia.

Malnutrition and related complications can also arise when swallowing impairment leads to fear of choking on food and liquids, slowed rate of consumption, and self-limited food choices. If uncorrected, inadequate nutritional intake exacerbates dysphagia as the muscles that help facilitate normal swallow weaken as physiological reserves are depleted. Malnutrition is associated with having a more than 3-times greater risk of infection. Infections are common in individuals with neurodegenerative diseases (thus, likely to have a chronic swallowing impairment that jeopardizes dietary adequacy). The conditions of Alzheimer's disease, Parkinson's disease, and multiple sclerosis account for nearly 400,000 U.S. hospital discharges annually, and up to 32% of these patients suffer urinary tract infection.

Malnutrition has serious implications for patient recovery. Malnourished patients have longer length of hospital stay, are more likely to be re-hospitalized, and have higher costs for hospital care. Having malnutrition as the principal diagnosis is associated with a mean 8 day length of hospital stay and nearly $22,000 in costs for hospital care. Furthermore, malnutrition leads to unintentional loss of weight and predominant loss of muscle and strength, ultimately impairing mobility and the ability to care for oneself. With the loss of functionality, caregiver burden becomes generally more severe, necessitating informal caregivers, then formal caregivers, and then institutionalization. However, malnutrition is an avoidable clinical complication of dysphagia.

Considering the prevalence of dysphagia, possible complications related thereto, and the costs associated with same, it would be beneficial to provide apparatuses and methods for detecting dysphagia earlier and more accurately. Such measures would stand to improve the lives of a large and growing number of persons with swallowing impairments.

SUMMARY

The present disclosure is related to apparatuses for detecting and/or diagnosing a swallowing disorder. In a general embodiment, an apparatus is provided and includes a disposable sensor base and a sensor. The disposable sensor base includes a sensor interface having a predetermined shape and a directionally-keyed mating surface. The sensor includes a handle portion having a shape that corresponds to the predetermined shape of the sensor interface, a support portion configured to be received by the directionally-keyed mating surface when the sensor is inserted into the sensor interface, and electronics configured to collect data sensed by the sensor. The sensor may be a device selected from the group consisting of an accelerometer, an acoustic device, or combinations thereof.

In an embodiment, the predetermined shape of the sensor interface is substantially semi-circular and the handle portion has a substantially cylindrical shape.

In an embodiment, the disposable sensor base further includes at least one cut-away portion so constructed and arranged to provide flexibility to the sensor base. The disposable sensor base may also have a curved shape on a side designed to contact a patient's neck so as to follow the anatomical shape of the patient's neck.

In an embodiment, the directionally-keyed mating surface extends into an interior portion of the sensor base such that the support portion of the sensor can slide into the directionally-keyed mating surface and fit fully within a perimeter of the disposable sensor base.

In an embodiment, the apparatus includes at least one disposable strap attached to the disposable sensor base. The disposable strap may be so constructed and arranged to attach the disposable sensor base to an individual using an attachment mechanism selected from the group consisting of an adhesive, velcro, a buckle, a hook and eye closure, a button, a snap, or combinations thereof. The disposable strap may also include a rail and the disposable sensor base may include at least one clasp that slidingly attaches to the rail.

In an embodiment, the electronics are configured to detect a swallowing condition typically associated with dysphagia. The electronics may include a printed circuit board in communication with a processing unit.

In another embodiment, an apparatus is provided and includes a disposable sensor base and a sensor. The disposable sensor base includes a sensor interface having a directionally-keyed mating surface with at least one notch. The sensor includes a handle portion, a support portion including a projection having a shape that corresponds to a shape of the notch such that the projection mates with the notch when the sensor is received by the sensor interface, and electronics configured to collect data sensed by the sensor.

In an embodiment, the projection is located on a bottom surface of the support portion. The directionally-keyed mating surface may extend into an interior portion of the disposable sensor base such that the support portion of the sensor can slide into the directionally-keyed mating surface and fit fully within a perimeter of the sensor base.

In an embodiment, the handle portion has a shape selected from the group consisting of cylindrical, rectangular, square, or combinations thereof.

In an embodiment, the apparatus includes at least one disposable strap attached to the sensor base. The disposable strap may be so constructed and arranged to attach the sensor base to an individual using an attachment mechanism selected from the group consisting of an adhesive, velcro, a buckle, a hook and eye closure, a button, a snap, or combinations thereof. The disposable strap may also include a rail and the disposable sensor base may include at least one clasp that slidingly attaches to the rail.

In an embodiment, the sensor further includes at least one groove on a top surface of the support portion that is configured to prevent movement of the sensor when the sensor is inserted into the disposable sensor base.

In an embodiment, the disposable sensor base may have a curved shape on a side designed to contact a patient's neck so as to follow the anatomical shape of the patient's neck.

In yet another embodiment, a method for detecting a swallowing disorder is provided. The method includes providing an apparatus having a disposable sensor base and a sensor. The disposable sensor base includes a sensor interface having a predetermined shape and a directionally-keyed mating surface. The sensor includes a handle portion having a shape that corresponds to the predetermined shape of the sensor interface, and a support portion configured to be received by the directionally-keyed mating surface when the sensor is inserted into the sensor interface. The method further includes attaching the apparatus to an individual's neck, and sensing, with the sensor, a physiological occurrence during an individual's swallow.

In an embodiment, the method further includes detecting a swallowing disorder if the physiological occurrence is sufficiently abnormal.

An advantage of the present disclosure is to provide improved diagnostic apparatuses.

Another advantage of the present disclosure is to provide apparatuses for detecting swallowing disorders.

Another advantage of the present disclosure is to provide apparatuses for detecting dysphagia.

Yet another advantage of the present disclosure is to provide easy-to-use, partially disposable diagnostic apparatuses.

Still yet another advantage of the present disclosure is to provide methods for detecting and/or diagnosing swallowing disorders.

Additional features and advantages are described herein, and will be apparent from the following Detailed Description and the figures.

DETAILED DESCRIPTION

As used in this disclosure and the appended claims, the singular forms "a," "an" and "the" include plural referents unless the context clearly dictates otherwise. Thus, for example, reference to "a polypeptide" includes a mixture of two or more polypeptides, and the like.

While the terms "individual" and "patient" are often used herein to refer to a human, the invention is not so limited. Accordingly, the terms "individual" and "patient" refer to any animal, mammal or human having or at risk for a medical condition that can benefit from the treatment or use of the apparatus.

The present disclosure relates to apparatuses that may be used to detect and/or diagnose swallowing disorders such as, but not limited to, dysphagia. The present disclosure also relates to methods for detecting and/or diagnosing swallowing disorders.

The normal swallowing of a human (or mammal) involves three distinct phases which are interdependent and well coordinated: (i) the oral, (ii) the pharyngeal, and (iii) the esophageal phases. In the oral phase, which is under voluntary control, food that has been chewed and mixed with saliva is formed into a bolus for delivery by voluntary tongue movements to the back of the mouth, into the pharynx. The pharyngeal phase is involuntary and is triggered by food/liquid bolus passing through the faucial pillars into the pharynx. Contraction of the three constrictors of the pharynx propels the bolus towards the upper esophageal sphincter. Simultaneously, the soft palate closes the nasopharynx. The larynx moves upwards to prevent food or liquid passing into the airway, which is aided by the backward tilt of the epiglottis and closure of the vocal folds. The esophageal phase is also involuntary and starts with the relaxation of the upper esophageal sphincter followed by peristalsis, which pushes the bolus down to the stomach.

Dysphagia refers to the symptom of difficulty in swallowing. General causes of dysphagia have been identified and include, but are not limited to a decreased ability to swallow, the tongue not exerting enough pressure on the soft palate, abnormal epiglottis behavior, etc. The consequences of untreated or poorly managed oral pharyngeal dysphagia can be severe, including dehydration, malnutrition leading to dysfunctional immune response, and reduced functionality, airway obstruction with solid foods (choking), and airway aspiration of liquids and semi-solid foods, promoting aspiration pneumonia and/or pneumonitis. Severe oral pharyngeal dysphagia may require nutrition to be supplied by tube feeding.

In a general embodiment, the present disclosure provides apparatuses for detecting and/or diagnosing swallowing disorders (e.g., dysphagia). The apparatuses of the present disclosure are designed to be in contact with a patient's throat to detect any swallowing disorders during the patient's swallow. In this respect, the apparatuses may be adhered to a patient's throat or may be configured as a collar, or straps, that can be tightened and adjusted around a patient's throat during testing. The skilled artisan will appreciate, however, that the apparatuses need not be adhered to, or fixed around a patient's throat and may be placed adjacent a patient's throat by any known means so long as the sensor of the apparatus is able to detect the necessary swallowing characteristics.

Figure 1:
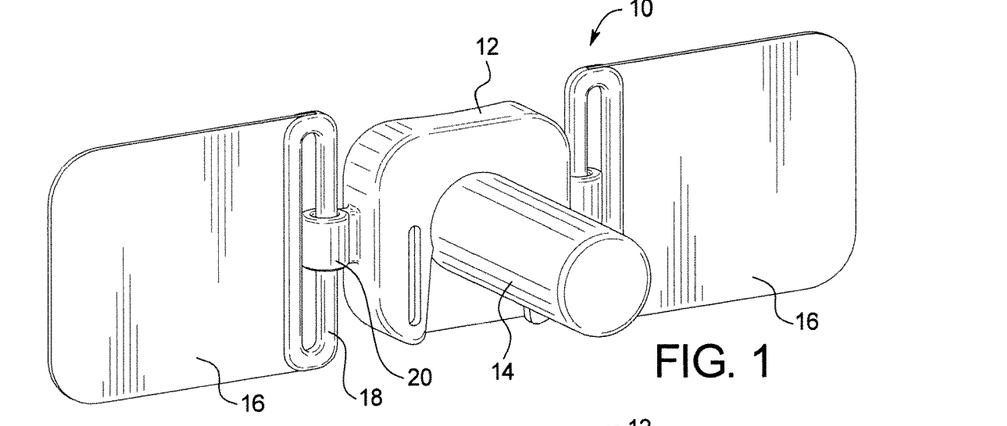
FIG. 1 shows a perspective view of an apparatus in accordance with an embodiment of the present disclosure.

As shown in FIG. 1, an apparatus 10 is provided and includes a sensor base 12, a sensor 14 that mates with sensor base 12, and flexible straps 16 attached to sensor base 12. Flexible straps 16 are attached to sensor base 12 by height adjustment rails 18, which are slideably connected to clasps 20 of sensor base 12 to provide optimal placement of sensor base 12 on a patient's throat during testing, regardless of the location of flexible straps 16. Alternatively, however, the skilled artisan will appreciate that apparatus 10 need not include height adjustment rails 18 and clasps 20. Instead, and in an alternative embodiment, sensor base 12 may be fixed to flexible strap(s) that do not provide for height adjustment. In another embodiment, sensor base 12 may include an adhesive, or other self-attaching means, and not require the use of any flexible strap(s) to attach the apparatus to a patient's neck.

In use, apparatus 10 may be affixed to a patient's through using flexible straps 16, which may include an adhesive to attach the apparatus, or may form a collar-type configuration where ends of flexible straps 16 connect via a connection means (e.g., velcro, adhesive, buckle, button, snap, hook and eye, etc.) to form close around a patient's neck. Adjustment of flexible straps 16 along or around a patient's neck keeps sensor base 12 in direct contact with the patient's throat such that sensor 14 is able to register the physiological occurrences described above in the patient's throat during swallowing. Sensor 14 can then transmit data to a processing unit that can interpret, store, and recall swallowing data (e.g., acceleration measurements) from the current patient, or previously tested patients. This data can then be useful in detecting and/or diagnosing potential swallowing disorders. In this regard, sensor 14 may be any apparatus that is capable of detecting and measuring the motion of a patient's hyoid bone. For example, sensor 14 may be an accelerometer, an acoustic device, or the like.

Figure 2:
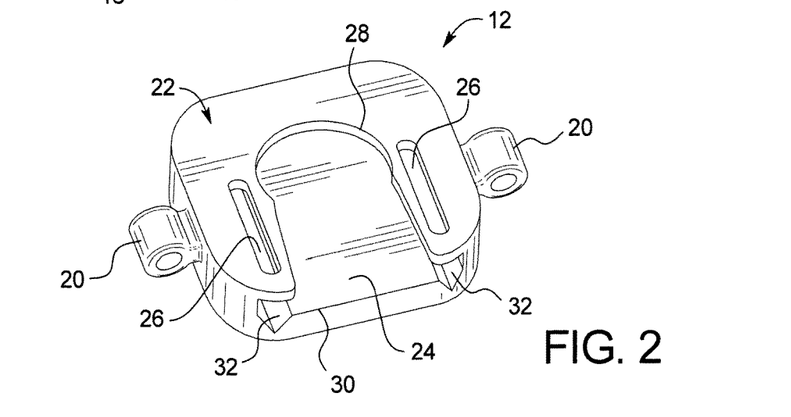
FIG. 2 shows a perspective view of a sensor base in accordance with an embodiment of the present disclosure.

Sensor base 12 may be manufactured from any known material useful in accepting and supporting a mated component (e.g., sensor 14). For example, sensor base 12 may be manufactured using any known plastic materials, light metals, or sturdy cardboard, card stock, paperboard, etc. Similarly, sensor base 12 may have any size or shape known in the art. For example, and as shown in FIG. 2, sensor base 12 may be substantially square shaped and may range in size from about one-half squared, to about 3 inches squared, or may be about 1 square inch, or about 2 square inches, or the like. Alternatively, sensor base 12 may be substantially rectangular, circular, or triangular in shape and may have any dimensions known in the art. Regardless of the exact size and shape, sensor base 12 should be sized and shaped to comfortably and directly contact a patient's throat during testing. In an embodiment, sensor base 12 may be slightly curved so as to anatomically/physiologically adapt to a patient's neck when sensor base 12 is in contact with a patient's neck. In this regard, a side of sensor base 12 that contacts patient's neck should be curved so as to follow the natural shape of the patient's curved neck. This shape allows sensor 14 to more closely track the motion of the hyoid bone during swallowing.

As shown in FIG. 2, a first surface 22 of sensor base 12 includes a sensor interface portion 24 and at least one slot 26, which provides a leaf-spring type function to afford sensor base 12 with flexibility to prevent damage to sensor base 12 during insertion of sensor 14, and to allow for easy insertion of sensor 14. A second surface (not shown) of sensor base 12, which is opposite first surface 22, may be substantially flat in order to comfortably and directly contact a patient's throat during testing. In an embodiment, the second surface of sensor base 12 may include an adhesive to ensure direct contact of sensor base 12 with the patient's throat during testing.

Sensor interface 24 of sensor base 12 is configured to mate with sensor 14. In this regard, sensor interface 24 is configured as a shaped cut-away portion 28 on first surface 22 having a directionally-keyed mating surface 30 that imposes orientational constraint, such as a slit located on a bottom side of sensor base 12. As used herein, a "cut-away" portion is a portion of a surface (e.g., first surface 22) that has been removed such that a remaining portion of the surface, or an outline of the cut-away portion, forms a shape. Additionally, as used herein, a "slit" refers to a portion of sensor base 12 that is removed from an interior portion of sensor base 12 (e.g., a hollow portion of sensor base 12). The directionally-keyed mating surface 30, such as a slit, may impose orientational constraint by imposing rotational and translational contraints. In an embodiment, slit 30 is a substantially rectangular shaped, hollow portion that extends into an interior, middle portion of sensor base 12 in a direction that is substantially parallel to first surface 22 of sensor base 12. In use, sensor 14 is slid into slit 30 and is snap-fit, or otherwise fit, into cut-away portion 28 on sensor interface 24.

To accommodate the mating of sensor 14 and sensor base 12, sensor interface 24 may have a shape that is wider at a bottom portion to easily accept sensor 14, and narrows or tapers to a predetermined shape that may be used, at least in part, to snap-fit sensor 14 in cut-away portion 28 of sensor interface 24. For example, and as shown in FIG. 2, sensor interface 24 is wider at a bottom portion and tapers inward and upward toward a substantially semi-circular shape that is so constructed and arranged to accept the shape of a substantially cylindrical sensor 14. The semi-circular shape, or a shape that is slightly more circular than semi-circular, of sensor interface 24 may be used to help snap-fit sensor 14 within sensor interface 24. Alternatively, the skilled artisan will appreciate that sensor interface 24 need not be limited to a shape that corresponds to a shape of sensor 14, but may have any shape known in the art.

As shown in FIG. 2, slit 30 of sensor base 12 may include one or more notched portions 32 that are so constructed and arranged to cooperate with one or more of a projection of sensor 14 as sensor 14 is slid into sensor base 12. In this regard, notched portions 32 ensure proper alignment of sensor 14 in sensor base 12. Notched portions 32 may also ensure that sensor bases 12 are only manufactured and sold for use with authorized sensors, which include correspondingly shaped projections, as will be discussed further below.

Sensor base 12 may also include at least one small projection (not shown) that extends downward from a top portion of slit 30 to interact with at least one indented portion 40 of sensor 14. The interaction of the small projection in slit 30 and indented portion 40 ensure that sensor 14 is securely and tightly fitted in sensor base 12 when sensor 14 and sensor base 12 are mated. In this regard, the small, downward extending projection presses downward onto indented portion 40, eliminating any free space in which sensor 14 can move. This presses sensor 14 securely against a bottom of slit 30 and prevents sensor 14 from moving after insertion or falling out of sensor base 12.

Figure 3:
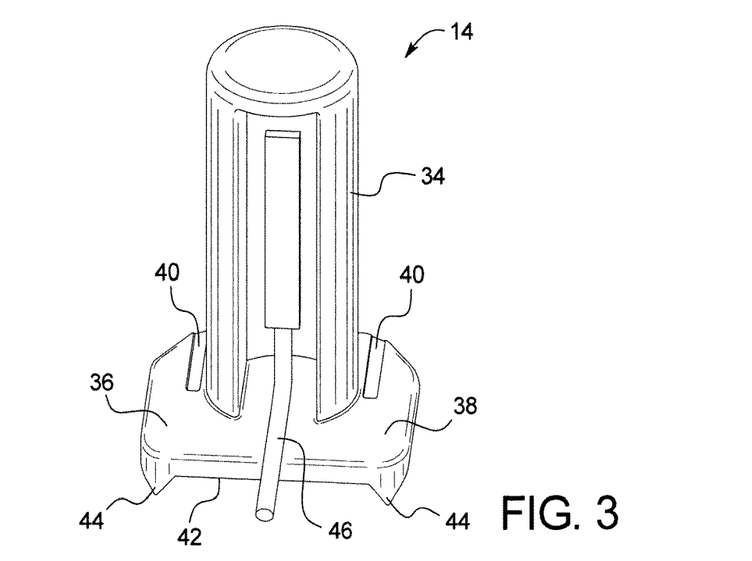
FIG. 3 shows a perspective view of a sensor in accordance with an embodiment of the present disclosure.

FIG. 3 illustrates an embodiment of a sensor 14 of the present disclosure, which includes a handle portion 34 and a support portion 36. Handle 34 may have any size and shape known in the art that is useful for gripping and handling during assembly of apparatus 10 and for ease of use during testing. In an embodiment, and as shown in FIG. 3, handle 34 may be substantially circular in cross-section such that handle 34 has an overall cylindrical shape. Regardless of the particular size and shape of handle 34, however, it should be sized and shaped to properly fit into sensor interface 24, as discussed above. For example, handle 34 of FIG. 3 has a substantially circular cross-section that is configured to mate with the substantially semi-circular shape of the upper portion of sensor interface 24. This corresponding fit helps to ensure a secure fit and proper alignment of sensor 14 in sensor base 12.

As shown in FIG. 3, support 36 of sensor 14 has a substantially flat top surface 38 including handle 34. In an embodiment, support 36 also includes an indentation 40 that is sized and shaped to mate with the small projections (not shown) on a top portion of slit 30 to ensure a secure fit and proper alignment of sensor 14 in sensor base 12. Indentation 40 may be any size or shape known in the art so long as indentation 40 correspondingly engages the small projections on a top portion of slit 30. For example, indentation 40 may be substantially elongated, or rectangular, in shape. Support 36 may include any number of indentations 40 including, for example, one, two, three, four or five indentations 40. In an embodiment, support 36 includes two, substantially rectangular indentations 40.

Support 36 also includes a bottom surface 42 having a projection 44 that is sized and shaped to mate with notches 32 of slit 30. Projection 44 may be any size or shape known in the art so long as projection 44 correspondingly engages notches 32. Due to the corresponding engagement of projection 44 with notch 32, projection 44 may be used to help guide sensor 14 into sensor base 12. Additionally, projection 44 may also ensure that sensors 14 are only manufactured and sold for use with authorized sensor bases, which include correspondingly shaped notches. Support 36 may include any number of projections 44 including, for example, one, two, three, four or five projections 44. In an embodiment, support 36 includes two projections 44 that mate with two notches 32 of slit 30.

In an embodiment, sensor 14 includes electronics 46 that are configured to transmit swallowing data from a patient to a processing unit. Electronics 46 may include, for example, a printed circuit board (not shown) in sensor 14, as well as wires or wireless transmitters to transmit the data collected during a swallowing test to a processing unit. The processing unit may be any suitable processing device that is able to provide and receive information and to execute instructions (e.g., computer programs). The processing unit may also be capable of accessing databases, manipulating data, calculating values and sending results of calculations to an output (e.g., display device, personal digital assistant, mobile wireless device, etc). By way of example one such device is an iPad available from Apple computers.

Figure 4:
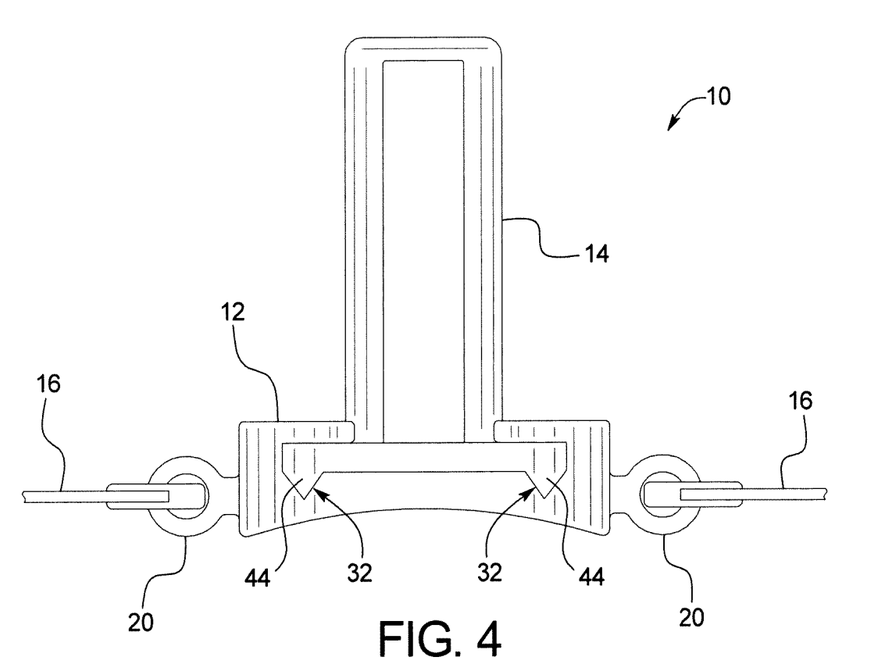
FIG. 4 shows a side view of the apparatus of FIG. 1 in accordance with an embodiment of the present disclosure.

FIG. 4 illustrates an assembled apparatus 10 that is ready to be used for a swallowing test. As shown in FIG. 4, sensor 14 has been slid into slit 30 of sensor base 12 and projections 44 are mated with notches 32. Sensor 14 may be inserted into sensor base 12 either before or after attachment of sensor base 12 to patient's neck or throat to perform a swallowing test. The patient's neck may be sterilized prior to placement of the apparatus on the patient's neck. In an embodiment, sensor base 12 may also include an arrow, dot, asterisk, target, or any other such indicator (not shown) to designate a location on sensor base 12 that should be positioned with respect to the patient's Adam's Apple (i.e., laryngeal prominence) to follow and/or mimic the motion of the hyoid bone in order to properly measure a signal amplitude during the swallowing test.

During the swallowing test, sensor 14 collects (and can transmit) data to a processing unit that is representative of a number of different characteristics of the patient's swallow (e.g., acceleration measurements, amplitudes, etc.). The data can be used to detect any abnormalities or inconsistencies of the patient's swallow, which can help to diagnose whether the patient has any swallowing disorders such as, for example, dysphagia.

After use in the patient swallowing test, the assembly of sensor base 12 and/or flexible straps 16 may be discarded or disposed of. For this reason, assemblies of sensor base 12 and/or flexible straps 16 may be made of less expensive materials that are disposable, biodegradable, etc. In contrast, sensors 14 include expensive electronics that are costly to replace. Thus, sensors 14 are likely to be made of more durable materials that are not disposable or biodegradable, or would be costly to replace. Due to the partially disposable nature of the devices, apparatuses 10 of the present disclosure provide the cost benefit of not requiring fully replacement before performing a swallowing test on a new patient. Instead, sensors 14 may be mated with new assemblies of sensor base 12 and/or flexible straps 16 and reused for a new patient swallowing test.

Figure 5:
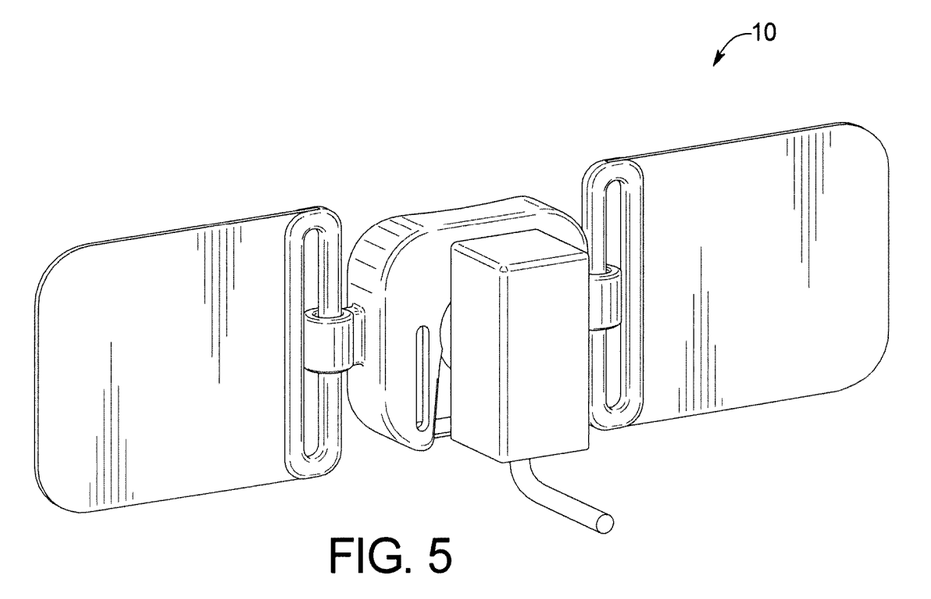
FIG. 5 shows a perspective view of an apparatus in accordance with an embodiment of the present disclosure.

FIG. 5 illustrates an alternative embodiment of an apparatus 10 of the present disclosure. In the alternative embodiment, the sensor includes a substantially rectangular-shaped handle that may be easier for certain patients, technicians, or physicians to use during testing.

Figure 6:
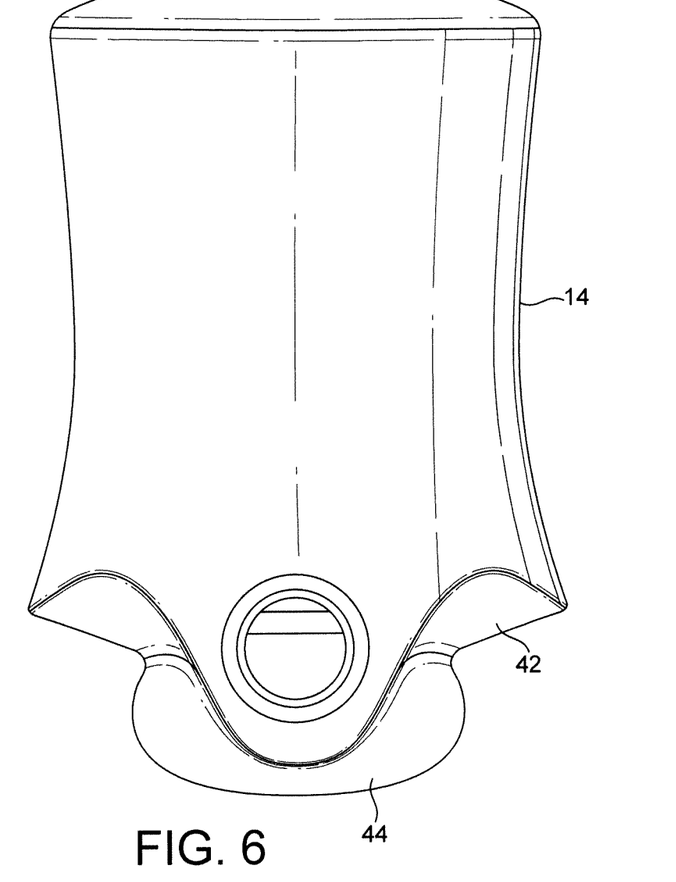
FIG. 6 shows a perspective view of a sensor in accordance with an embodiment of the present disclosure.
Figure 7:
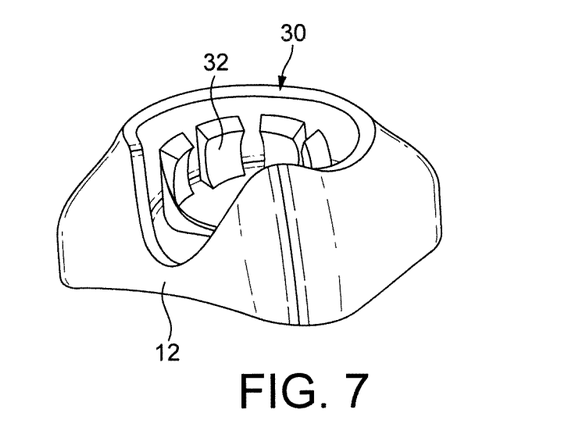
FIG. 7 shows a perspective view of a sensor base in accordance with an embodiment of the present disclosure.

FIGS. 6 and 7 illustrate an embodiment of an apparatus 10 of the present disclosure in which sensor interface 24 of sensor base 12 mates with sensor 14. A portion of sensor 14 may have a spherical shape, and the directionally-keyed mating surface 30 that imposes orientational constraint may receive the spherical portion of sensor 14. For example, projection 44 on bottom surface 42 of sensor 14 can have a substantially spherical shape, such as by being a dome, and the directionally-keyed mating surface 30 in sensor base 12 may be a slot having a shape that corresponds to the spherical shape of projection 44. The interaction of spherical projection 44 and directionally-keyed mating surface 30 ensure that sensor 14 is securely and tightly fitted in sensor base 12 when sensor 14 and sensor base 12 are mated. In an embodiment, spherical projection 44 can form support portion 36, and a portion of sensor 14 above the spherical projection 44 can form handle portion 34.

Directionally-keyed mating surface 30 may be formed in a portion of sensor base 12 that is removed from an interior portion of sensor base 12 (e.g., a hollow portion of sensor base 12). Directionally-keyed mating surface 30 may be a hollow portion that extends into an interior, middle portion of sensor base 12 and is configured to receive and mate with spherical projection 44 of sensor 14. In use, sensor 14 slides into directionally-keyed mating surface 30 and is snap-fit, or otherwise fit, into directionally-keyed mating surface 30.

One or more notched portions 32 of directionally-keyed mating surface 30 may be constructed and arranged to receive rounded lateral surfaces of spherical projection 44 as sensor 14 slides into sensor base 12. In this regard, one or more notched portions 32 ensure proper alignment of sensor 14 in sensor base 12. Notched portions 32 may also ensure that sensor bases 12 are only manufactured and sold for use with authorized sensors.

In still yet another embodiment, methods for detecting and/or diagnosing a swallowing disorder are provided. The methods include providing an apparatus of the present disclosure, attaching the apparatus to the neck of a patient, and performing a swallowing test. The methods may further include sliding a sensor into a sensor interface of a sensor base, adjusting the height of a sensor base along height adjustment rails of an apparatus strap, adhering a sensor base to the patient's neck, collecting swallowing data, transmitting swallowing data, analyzing swallowing data, and diagnosing a swallowing disorder if a detected physiological swallowing occurrence or characteristic is sufficiently abnormal.

By using the improved apparatuses and methods of the present disclosure, swallowing disorders can be more easily detected and/or diagnosed, which provides patients with numerous physical, emotional and economical benefits. Such advantages include, but are not limited to early detection of a swallowing disorder, earlier treatment of a swallowing disorder, an overall healthier condition of the patient, prevention of further health-related decline, and reduced medical costs associated with swallowing disorders.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An apparatus for testing a patient, the apparatus comprising:
   a disposable sensor base comprising a first side and a second side, the disposable sensor base comprising a sensor interface having a predetermined shape and a directionally-keyed mating surface, the sensor interface comprising a slit in the sensor base that comprises one or more notched portions, the directionally-keyed mating surface configured to impose orientational constraint; and
   a sensor comprising
     a handle portion configured to be gripped and handled during assembly of the apparatus, the handle portion having a shape that corresponds to the predetermined shape of the sensor interface,
     a support portion comprising one or more projections, the support portion configured to be received by the directionally-keyed mating surface when the sensor is inserted into the sensor interface, the one or more projections configured to cooperate with the one or more notch portions when the sensor is inserted into the interface, and
     electronics configured to collect data sensed by the sensor, the disposable sensor base is sized and shaped to contact the patient such that during the testing the first side contacts the patient and is distanced from the sensor, and the second side mates with the sensor and is distanced from the patient.

2. The apparatus of claim 1, wherein the predetermined shape of the sensor interface is substantially semi-circular and the handle portion has a substantially cylindrical shape.

3. The apparatus of claim 1, wherein the disposable sensor base comprises at least one slot that is constructed and arranged to provide flexibility to the disposable sensor base.

4. The apparatus of claim 1, wherein the directionally-keyed mating surface extends into an interior middle portion of the disposable sensor base such that the support portion of the sensor can slide into the directionally-keyed mating surface and fit fully within a perimeter of the disposable sensor base.

5. The apparatus of claim 1 comprising at least one disposable strap attached to the disposable sensor base, the disposable strap is constructed and arranged to attach the disposable sensor base to an individual using an attachment mechanism selected from the group consisting of an adhesive, velcro, a buckle, a hook and eye closure, a button, a snap, and combinations thereof.

6. The apparatus of claim 5, wherein the disposable strap includes a rail and the disposable sensor base includes at least one clasp that slidingly attaches to the rail.

7. The apparatus of claim 1, wherein the first side of the disposable sensor base comprises a curved shape configured to contact a patient's neck so as to follow an anatomical shape of the patient's neck.

8. The apparatus of claim 1, wherein the sensor comprises a device selected from the group consisting of an accelerometer, an acoustic device, and combinations thereof.

9. The apparatus of claim 1, wherein the electronics are configured to detect a swallowing condition typically associated with dysphagia.

10. An apparatus for testing a patient, the apparatus comprising:
    a disposable sensor base comprising a first side and a second side, the disposable sensor base comprising a sensor interface having a directionally-keyed mating surface, the sensor interface comprising a slit in the sensor base that comprises one or more notched portions, the directionally-keyed mating surface configured to impose orientational constraint; and
    a sensor comprising
      a handle portion,
      a support portion comprising one or more projections configured to cooperate with the one or more notch portions when the sensor is inserted into the interface, and
      electronics configured to collect data sensed by the sensor, the disposable sensor base is sized and shaped to contact the patient such that during the testing the first side contacts the patient and is distanced from the sensor, and the second side mates with the sensor and is distanced from the patient.

11. The apparatus of claim 10, wherein the disposable sensor base further comprises at least one slot, and the support portion comprises at least one indented portion having a shape that corresponds to a shape of the at least one slot, the at least one indented portion configured to cooperate with the at least one slot when the sensor is inserted into the interface, and
    wherein the at least one indented portion and the handle portion are on a top surface of the support portion, and the one or more projections are located on a bottom surface of the support portion, wherein the top surface faces a first direction and the bottom surface faces a second direction opposite from the first direction, and
    wherein the interface is configured for the sensor to insert into the interface in a third direction, the third direction perpendicular to the first direction and the second direction.

12. The apparatus of claim 10, wherein the directionally-keyed mating surface extends into an interior middle portion of the disposable sensor base such that the support portion of the sensor can slide into the directionally-keyed mating surface and fit fully within a perimeter of the disposable sensor base.

13. The apparatus of claim 10, wherein the handle portion has a shape selected from the group consisting of cylindrical, rectangular, square, and combinations thereof.

14. The apparatus of claim 10 further comprising at least one disposable strap attached to the disposable sensor base, the disposable strap is constructed and arranged to attach the disposable sensor base to an individual using an attachment mechanism selected from the group consisting of an adhesive, velcro, a buckle, a hook and eye closure, a button, a snap, and combinations thereof.

15. The apparatus of claim 10, wherein the first side of the disposable sensor base comprises a curved shape configured to contact a patient's neck so as to follow an anatomical shape of the patient's neck.

16. The apparatus of claim 14, wherein the disposable strap includes a rail and the disposable sensor base includes at least one clasp that slidingly attaches to the rail.

17. The apparatus of claim 10, wherein the sensor further includes at least one indentation on a top surface of the support portion that is configured to prevent movement of the sensor when the sensor is inserted into the disposable sensor base.

18. A method for detecting a swallowing disorder, the method comprising:
   using an apparatus for testing a patient, the apparatus comprising
   a disposable sensor base comprising a first side and a second side, the disposable sensor base comprising a sensor interface having a predetermined shape and a directionally-keyed mating surface, the sensor comprising a slit in the sensor base that comprises one or more notched portions, the directionally-keyed mating surface configured to impose orientational constraint, and a sensor comprising a handle portion configured to be gripped and handled during assembly of the apparatus, the handle portion having a shape that corresponds to the predetermined shape of the sensor interface, and a support portion comprising one or more projections, the support portion configured to be received by the directionally-keyed mating surface when the sensor is inserted into the sensor interface, the one or more projections configured to cooperate with the one or more notch portions when the sensor is inserted into the interface, the disposable sensor base is sized and shaped to contact the patient such that during the testing the first side contacts the patient and is distanced from the sensor, and the second side mates with the sensor and is distanced from the patient;
   attaching the apparatus to an individual's neck; and
   sensing, with the sensor, a physiological occurrence during an individual's swallow.

19. The method of claim 18, further comprising diagnosing a swallowing disorder based on the physiological occurrence.

20. The method of claim 18, further comprising disconnecting the disposable sensor base from the sensor after a single use of the apparatus;
   discarding the disposable sensor base;
   attaching a second disposable sensor base to the sensor; and
   diagnosing a new patient using the sensor attached to the second disposable sensor base.

* * * * *